(12) United States Patent
Schampers et al.

(10) Patent No.: US 9,142,384 B2
(45) Date of Patent: Sep. 22, 2015

(54) METHOD OF WELDING A FROZEN AQUEOUS SAMPLE TO A MICROPROBE

(71) Applicant: FEI Company, Hillsboro, OR (US)

(72) Inventors: Rudolf Johannes Peter Gerardus Schampers, Tegelen (NL); Johannes Antonius Hendricus Wilhelmus Gerardus Persoon, Waalre (NL); Andreas Theodorus Engelen, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/302,024

(22) Filed: Jun. 11, 2014

(65) Prior Publication Data

US 2014/0367571 A1    Dec. 18, 2014

(30) Foreign Application Priority Data

Jun. 14, 2013  (EP) .................................. 13172127

(51) Int. Cl.
*H01J 37/20* (2006.01)
*H01J 37/26* (2006.01)
*G01N 1/28* (2006.01)
*G01N 1/42* (2006.01)
*G02B 21/32* (2006.01)
*H01J 37/315* (2006.01)

(52) U.S. Cl.
CPC . *H01J 37/20* (2013.01); *G01N 1/28* (2013.01); *G01N 1/42* (2013.01); *G02B 21/32* (2013.01); *H01J 37/315* (2013.01); *H01J 37/26* (2013.01); *H01J 2237/002* (2013.01); *H01J 2237/2065* (2013.01); *H01J 2237/31744* (2013.01); *H01J 2237/31745* (2013.01)

(58) Field of Classification Search
CPC ............. H01J 2237/31745; H01J 2237/31749; H01J 2237/2001; H01J 2237/204; H01J 2237/2007; H01J 2237/208; H01J 37/185; H01J 37/26; H01J 2237/206; H01J 2237/2002; H01J 2237/2065; H01J 37/31; H01J 37/315; H01J 37/20; H01J 2237/002; H01J 2237/31744; G01N 1/42; G01N 1/28; G02B 21/32
See application file for complete search history.

(56) References Cited

U.S. PATENT DOCUMENTS 7,227,140 B2 *  6/2007  Skidmore et al. ............. 250/307
8,513,622 B2 *  8/2013  Hartfield .................. 250/440.11
8,674,323 B2    3/2014  Schampers et al.
(Continued)

FOREIGN PATENT DOCUMENTS

EP    2009422 A1    12/2008
EP    2402477 A1    1/2012
(Continued)

*Primary Examiner* — Michael Logie
(74) *Attorney, Agent, or Firm* — Scheinberg & Associates, PC; Michael O. Scheinberg; John E. Hillert

(57) ABSTRACT

The invention relates to a method of welding a vitreous biological sample at a temperature below the glass transition temperature of approximately −137° C. to a micromanipulator, also kept at a temperature below the glass transition temperature. Where prior art methods used IBID with, for example, propane, or a heated needle (heated resistively or by e/g/laser), the invention uses a vibrating needle to locally melt the sample. By stopping the vibration, the sample freezes to the micromanipulator. The heat capacity of the heated parts is small, and the amount of material that stays in a vitreous condition thus large.

19 Claims, 2 Drawing Sheets

(56) References Cited

U.S. PATENT DOCUMENTS

| | | |
|---|---|---|
| 8,754,384 B1 | 6/2014 | Persoon et al. |
| 8,796,646 B2 * | 8/2014 | Mulders et al. ............ 250/492.1 |
| 8,884,248 B2 | 11/2014 | Mulders et al. |
| 2003/0089852 A1 * | 5/2003 | Ochiai et al. ................. 250/310 |
| 2004/0129878 A1 * | 7/2004 | Tomimatsu et al. .......... 250/307 |
| 2007/0131249 A1 * | 6/2007 | Nakaue ............................ 134/6 |
| 2009/0000400 A1 * | 1/2009 | Hayles et al. .............. 73/863.12 |
| 2009/0019877 A1 * | 1/2009 | Larson et al. .................. 62/320 |
| 2012/0003394 A1 * | 1/2012 | Mulders et al. ............... 427/551 |
| 2012/0024086 A1 * | 2/2012 | Stabacinskiene et al. . 73/864.91 |
| 2012/0286175 A1 * | 11/2012 | Searle et al. ................ 250/492.3 |
| 2013/0014528 A1 * | 1/2013 | Stabacinskiene et al. ...... 62/129 |
| 2013/0037706 A1 * | 2/2013 | Ditto .............................. 250/282 |
| 2013/0091875 A1 * | 4/2013 | Hartfield .......................... 62/62 |

FOREIGN PATENT DOCUMENTS

| | | |
|---|---|---|
| WO | 2005031789 A2 | 4/2005 |
| WO | 2012138738 A2 | 10/2012 |
| WO | 2012155044 A1 | 11/2012 |

* cited by examiner

METHOD OF WELDING A FROZEN AQUEOUS SAMPLE TO A MICROPROBE

The invention relates to a method of welding a sample to a microprobe, the method comprising the steps of:
  providing the sample;
  providing a microprobe with an extremity;
  moving the extremity to the sample until contact is made;
  locally melt the sample while a part of the sample is kept solidified; and
  freezing the locally melted sample to the extremity.

The invention further relates to an apparatus equipped to perform said method.

This method is known from European Patent No. EP2009422B1.

The known method describes a method where a microprobe with a sharp extremity at a cryogenic temperature is brought in contact with a frozen aqueous sample, such as a vitrified biological sample. The extremity is then temporarily heated to a temperature above the melting point of water. The heating is achieved by, for example, resistive heating, or heating with a laser beam. Following this the extremity is allowed to cool down again, as a result of which the aqueous sample freezes to the extremity. The heating and cooling is done sufficiently quick that at least part of the sample is kept in a frozen condition, more specifically in a vitrified condition.

Such a vitrified sample can, for example, be biological tissue to be inspected in an electron microscope. Such samples are often excavated from a larger part using a Focused Ion Beam apparatus and then, using the microprobe, transported to a sample carrier for further inspection.

A disadvantage of the known method is that due to the heat capacity of the heated part of the extremity a part of the sample melts, or loses its vitrified condition.

There is a need for a welding method where a smaller part of the sample is melted or where it loses its vitrified condition.

To that end the method according to the invention is characterized in that the local melting is achieved by vibration of the extremity, the locally melted sample freezing to the extremity when the vibration is stopped.

By vibration of the extremity the extremity and the frozen sample are rubbed over each other. This rubbing causes the frozen sample to locally melt. When the rubbing is then stopped, the melted part of the sample then freezes to the extremity. Because only the sample and the extremity are heated by the rubbing, the heat induced by the rubbing is transported away quickly, most of it in the part to which the extremity borders and that is kept to a low temperature (below the melting point of the sample material).

It is noted that another method is known from European Patent Application EP2402477A1. In this known method the sample is placed in the sample chamber of an apparatus equipped with a focused ion beam column producing a finely focused beam of ions and a gas injection system a jet of a gas with a melting point below the melting point of the sample. The gas molecules adhered to the sample are split in a part that bonds to the sample and a volatile part that is pumped from the sample chamber. An example of a gas used is propane, producing a carbon bond between sample and extremity.

A disadvantage of this method is the need for an ion beam column and a gas injection system for welding the sample to the extremity.

In an embodiment the solid sample is a frozen aqueous sample, a vitrified aqueous sample or a polymer.

Such samples are of great interest in electron microscopy, where they are also known as "biological samples". In electron microscopy these samples encompass cells, cell fragments, bacteria, viruses, enzymes and proteins.

In a preferred embodiment the sample is a vitrified aqueous sample or a vitrified polymer, the sample is provided at a temperature below the glass transition temperature of the sample, and a part of the sample is kept below the glass transition temperature of the sample material throughout the method, as a result of which part of the sample stays vitrified.

Particularly the use of the method to attach vitrified biological samples (either aqueous or polymers) to a microprobe proved to be effective. Vitrified biological samples are often used in cryo-electron microscopy (cryo-EM), more specifically cryo-transmission electron microscopy (cryo-TEM), as vitrified ice and vitrified polymers do not show crystals that can damage biological structures, such as membranes.

In yet another embodiment the extremity is a metal extremity.

A microprobe is typically equipped with a metal extremity, a needle of, for example, tungsten or tungsten/nickel.

In yet another embodiment the extremity is vibrating while contact is made.

This embodiment enables to observe exactly when the contact takes place, as then the amplitude of the vibration changes.

In yet another embodiment the frequency of the vibration is between 1 and 100 kHz.

These are frequencies that are easily achieved with, for example, piezo-actuators. Preferably a frequency is chosen where, in contact, an anti-node occurs, so that maximum energy transfer occurs.

In yet another embodiment the amplitude of the vibration is between 10 and 200 nm.

In yet another embodiment the extremity vibrates in the plane parallel to the surface of the sample.

This embodiment describes that the extremity is rubbed over the sample, instead of tapping the sample. In both modes energy is transferred and a local melt is achieved, but rubbing proved to be more controllable.

In yet another embodiment the welding takes place in an evacuated chamber, more specifically in the sample chamber of a charged particle apparatus Evidently the method must be performed in a non-condensing environment. Especially for temperatures below the glass transition temperature of water an evacuated chamber is preferred.

In a further embodiment the charged particle apparatus comprises an electron column and/or a focused ion beam column.

By equipping the charged particle apparatus with a focused ion beam column enables the apparatus to perform focused ion beam milling or -etching. Although the ion beam can be used for imaging the sample, and thus the process, a SEM column is preferred due to its higher signal-to-noise ratio and its higher resolution.

In an aspect of the invention a microprobe for use with a charged particle apparatus, the charged particle apparatus showing a sample position equipped to hold a sample, the microprobe showing an extremity, the microprobe equipped with positioning means to bring the extremity in contact with the sample, is characterized in that the extremity is equipped to vibrate, the extremity when vibrating locally melting the sample, the locally melted sample freezing to the extremity when the vibration is stopped.

In a further embodiment of the microprobe the extremity is equipped to be cooled to a temperature below −50° C., more specifically below the glass transition temperature of vitreous ice.

In yet another embodiment a charged particle apparatus equipped with a focused ion beam column and/or an electron beam column, a sample position equipped to hold a vitrified biological sample at a cryogenic temperature, the charged particle apparatus equipped with a microprobe of showing an extremity, the microprobe equipped with positioning means to bring the extremity in contact with the sample, the extremity is equipped to vibrate, the extremity when vibrating locally melting the sample, the locally melted sample freezing to the extremity when the vibration is stopped.

In a further embodiment the charged particle apparatus is equipped to keep the sample at a temperature below −50° C., more specifically below the glass transition temperature of vitreous ice, and the microprobe the extremity is equipped to be cooled to a temperature below −50° C., more specifically below the glass transition temperature of vitreous ice.

The invention is now elucidated using figures, in which identical reference numerals refer to corresponding features.

To that end:

This exemplary embodiment is used to attach a vitrified sample to a manipulator.

In step 1 a vitrified work piece is introduced in a dual beam apparatus with a cooled stage. A vitrified work piece can be made by plunging a thin work piece in a cryogenic liquid, such as propane, or by high pressure freezing, both methods known per se. To keep the sample vitrified, the sample should be kept below the glass transition temperature of water, approximately −137° C., implying that the stage should be kept at a low temperature, and that cryo-shields should be present to keep the sample from warming up. Often stage and cryo-shields are cooled with braids that lead to a cold-sink kept at liquid nitrogen temperature.

In step 2 the sample is excavated from the work piece. Typically this is done by ion beam milling. Often the sample is kept attached via a bridge to the work piece at one position and then in a later stage broken from the work piece or, alternatively, the bridge is milled away. The milling may be performed while an etchant is directed to the work piece, the etchant enhancing the milling rate or enhance the milling in a preferential direction.

In step 3 the microprobe is brought in contact with the sample. The microprobe may at that moment already be vibrating. An advantage of bringing an already vibrating microprobe in contract with the sample is that it is easy to observe when the extremity contacts the sample as this causes a change in amplitude.

In step 4 the microprobe is rubbing the sample. It is noted that the extremity (the needle) need not behave as a rigid unit, and that nodes and anti-nodes may occur. It should then be observed that in contact the extremity does not coincide with a node, as then no or little energy is generated at the rubbing spot.

It is further noted that typically the melting cannot be observed, and the rubbing time is based on experimental data. In the test vehicle in which the inventors performed experiments a rubbing time of 2 to 5 seconds was found satisfactory at a vibration frequency of 20 kHz and a vibration amplitude of 50 nm.

In step 5 the rubbing is stopped and the sample is allowed to freeze round the extremity of the microprobe.

In step 6 the sample is removed from the work piece. For further inspection the sample may, for example, be moved to a sample carrier for a TEM, or the sample may be thinned and then placed on a sample carrier.

Figure 1:
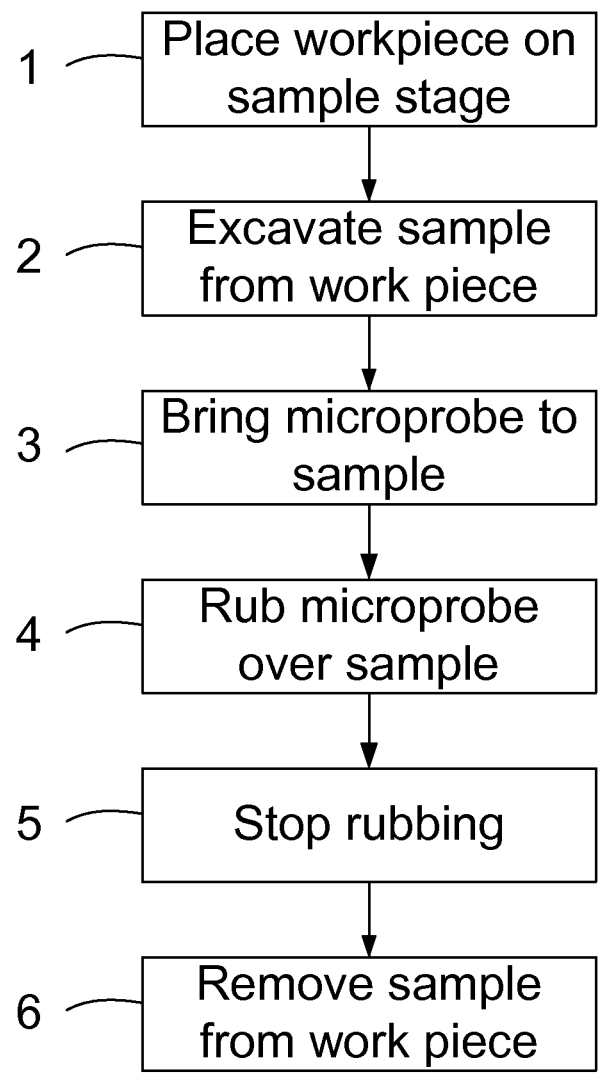
FIG. 1 shows a flowchart illustrating an exemplary embodiment of the method.
Figure 2:
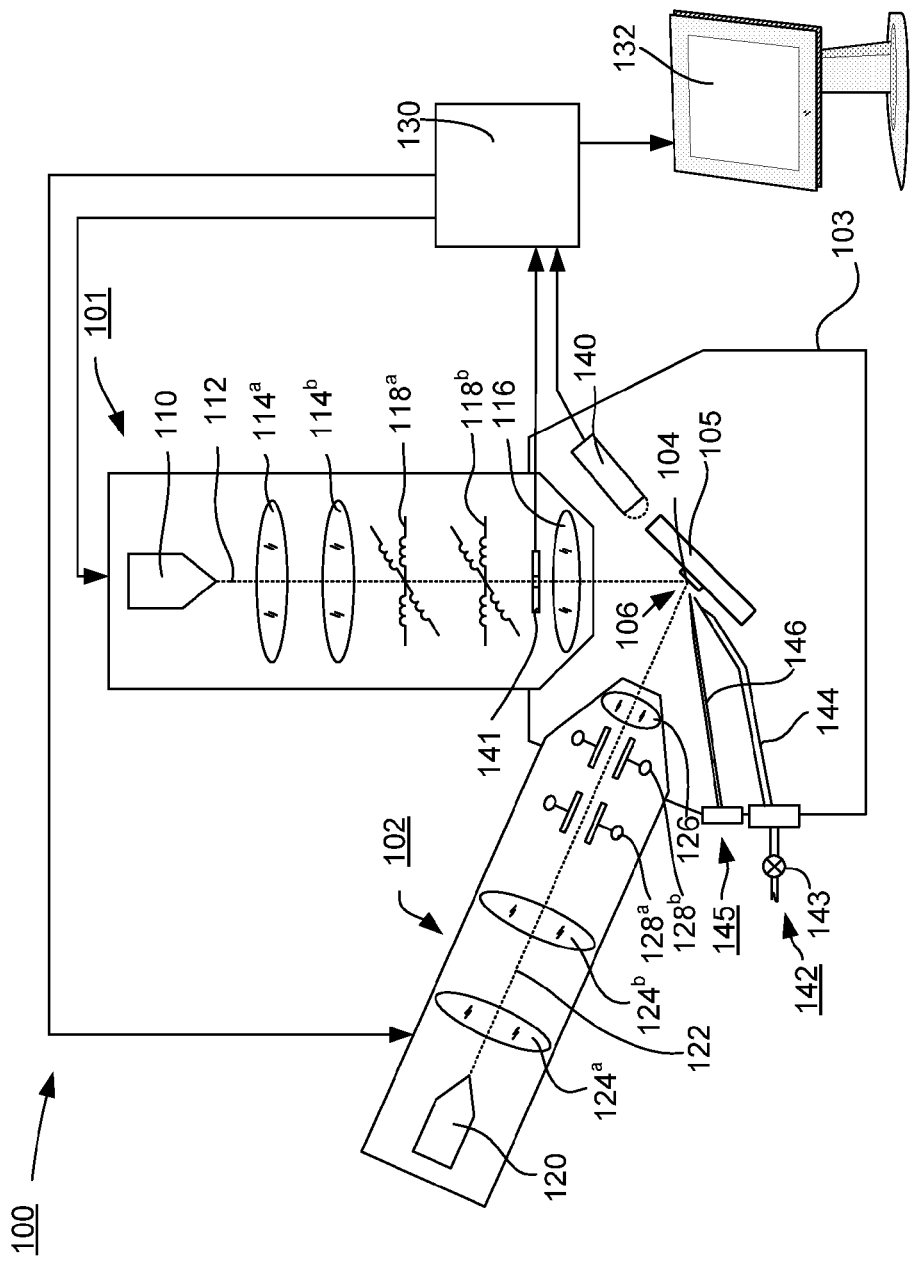
FIG. 2 shows a diagram illustrating an exemplary embodiment of the charged particle apparatus.

FIG. 2 depicts an exemplary dual beam SEM/FIB system 100 that is equipped to carry out a method according to the present invention. Suitable dual beam systems are commercially available, for example, from FEI Company, Hillsboro, Oreg., the assignee of the present application. While an example of suitable hardware is provided below, the invention is not limited to being implemented in any particular type of hardware.

The dual beam system 100 has a vertically mounted electron beam column 101 and a focused ion beam (FIB) column 102 mounted at an angle of approximately 52 degrees from the vertical on an evacuable sample chamber 103. The sample chamber may be evacuated by e.g. a turbo-molecular pump, or other known pumping means such as oil diffusion pumps, ion getter pumps, scroll pumps, etc. (not shown).

The electron beam column 101 comprises an electron source 110 for producing a beam of electrons 112. Electron-optical condenser lenses $114^a$, $114^b$ and objective lens 116 are used to finely focus the beam of electrons on a sample 104. Objective lens 116 comprises an electrostatic immersion lens, and preferably also a magnetic lens, so that the beam of electrons 112 is focused by both the electrostatic immersion field and the magnetic field. The beam of electrons can be positioned on and can be scanned over the surface of a sample (also known as substrate) 104 by means of deflections coil $118^a$ and $118^b$. It is noted that lenses and deflection unit may use electric fields to manipulate the electron beam, or that magnetic fields may be used, or a combination thereof.

Dual beam system 100 also includes focused ion beam (FIB) column 102 which comprises an ion source 120 for producing a beam of ions. Ion-optical condenser lenses $124^a$, $124^b$ and objective lens 126 are used to finely focus the beam of ions onto the sample 104. The beam of ions can be positioned on and scanned over the surface of the sample 104 by means of deflectors $128^a$ and $128^b$. Due to the nature of ions (mass over charge ratio) the lenses and deflectors are typically electrostatic in nature.

Electron beam 112 and ion beam 122 can be focused onto sample 104, which is mounted on a flat side of a sample manipulator in the form of a movable X-Y-Z stage 105 within vacuum chamber 103.

Column 101 and 102 are aligned to form an intersect 106 between ion beam 122 and electron beam 112. Preferably the sample is positioned at this intersect.

Mounted on the vacuum chamber is a (retractable) Gas Injection System (GIS) 142. The GIS comprises a reservoir (not shown) for holding the precursor material and a needle 144 for directing the precursor material to the surface of the substrate. The GIS further comprises means for regulating the supply of precursor material to the substrate. In this example the regulating means are depicted as an adjustable valve 143, but the regulating means may also take the form of e.g. controlled heating of the precursor material.

Mounted on the vacuum chamber is further a retractable and positional micromanipulator 145, comprising a tip 146 with a distal end located in the vacuum chamber. The distal part of tip 146 is for example used to probe the sample, or to adhere a (part of) the sample using, for example, Beam Induced Deposition (either using ion-, electron- or laser beams).

When the electrons in the electron beam strike sample 104, secondary electrons (SE's) and backscattered electrons (BSE's) are emitted. SE's are often defined as electrons emitted from the sample with an energy of less than 50 eV, while BSE's are often defined as electrons emitted from the sample with an energy in excess of 50 eV. At least part of the SE's and BSE's are detected by electron detector 140, such as an Everhard-Thornley detector, or an in-column detector mounted in-column, more preferably mounted within objective lens 116, the detector capable of detecting low energy electrons and backscattered electrons. It is noted that such a detector can be scintillator based or can be formed as semiconductor devices, and that such a detector can be segmented or not.

It is noted that, beside SE's and BSE's, also other types of radiation are emitted, such as X-rays, visible light, etc. These types of radiation may also be detected using appropriate detectors.

The signals of the detectors are fed to a system controller 130. Said system controller also controls the deflector signals, lenses, electron source, GIS, stage and pump(s), and other items of the instrument, including GIS system 142 and micromanipulator 145. The system controller can thus direct both the ion beam and the electron beam to specific locations on the sample, either using scan patterns or steady state deflection more. Using the positional information of the beam, and using the information of the detectors, the controller can form an image of the sample on the monitor.

It is noted that the system controller also controls the detectors, for example by controlling their gain.

It is noted that the in-column detector 141 shows a central through hole for passing the beam of electrons 112.

It is further noted that a detector such as detector 140 can be positional in the vacuum chamber, either to optimize detection efficiency or to make space for other parts during certain observation, the observations for example demanding another type of detector.

Stage 105 can support a sample and/or one or more TEM sample holders so that a minute part of a sample can be extracted from the sample and moved to a TEM sample holder. Stage 105 can preferably move in a horizontal plane (X and Y axes) and vertically (Z axis), and its temperature can be lowered due to cooling means (not shown), that may comprise. For example, braids thermally connecting the stage with a liquid nitrogen dewar. Stage 105 can also tilt approximately sixty (60) degrees or more and rotate about the Z axis. In some embodiments, a separate TEM sample stage (not shown) can be used.

Pumps are used to evacuate the electron beam column 101, the ion beam column 102 and the vacuum chamber 103. The vacuum pumps typically provide within chamber 103 a vacuum of approximately $3 \times 10^{-6}$ mbar. When a suitable precursor gas is introduced onto the sample surface, the chamber background pressure may rise, typically to about $5 \times 10^{-5}$ mbar. However, it is known to use pressures as high as 1-10 mbar, enabling the observation and "machining" of wet samples.

The micromanipulator 145, such as the AutoProbe 200™ from Omniprobe, Inc., Dallas, Tex., or the Model MM3A from Kleindiek Nanotechnik, Reutlingen, Germany, can precisely move objects within the vacuum chamber. The micromanipulator may comprise precision electric motors positioned outside the vacuum chamber to provide X, Y, Z, and theta control of a distal end positioned within the vacuum chamber. The micromanipulator can be fitted with different end effectors for manipulating small objects. In the embodiments described herein, the end effector is a thin probe. As is known in the prior art, a micromanipulator (or microprobe) can be used to transfer a TEM sample (which has been freed from a substrate, typically by an ion beam) to a TEM sample holder for analysis.

The micromanipulator 145, or microprobe, is adapted with cooling means (braids connected to a cold sink at liquid nitrogen temperature) and piezo actuators enabling the tip (end effector) to oscillate (vibrate) at the required frequency and amplitude. Hereby the micromanipulator as standardly available is changed into a micromanipulator according to the invention.

It is noted that, when observing for example polymers, instead of cooling to liquid nitrogen temperature cooling with a Peltier element to a temperature of, for example, −50° C. may suffice. This method may also be used at still higher temperatures (room temperature and above), but here IBID is an already well proven and well accepted technique.

In a preferred embodiment the invention thus relates to a method of welding a vitreous biological sample at a temperature below the glass transition temperature of approximately −137° C. to a micromanipulator, also kept at a temperature below the glass transition temperature. Where prior art methods used IBID with, for example, propane, or a heated needle (heated resistively or by e/g/laser), the invention uses a vibrating needle to locally melt the sample. By stopping the vibration, the sample freezes to the micromanipulator. The heat capacity of the heated parts is small, and the amount of material that stays in a vitreous condition thus large.

We claim as follows:

1. A method of welding a sample to a microprobe, the method comprising:
    providing the sample;
    providing a microprobe with an extremity;
    moving the extremity to the sample until contact is made;
    locally melting the sample while a part of the sample is kept solidified; and
    freezing the locally melted sample to the extremity;
    wherein the local melting is achieved by vibration of the extremity, the locally melted sample freezing to the extremity when the vibration is stopped.

2. The method of claim 1 in which the solid sample is a frozen aqueous sample, a vitrified aqueous sample or a polymer.

3. The method of claim 1 in which the sample is a vitrified aqueous sample or a vitrified polymer, the sample is provided at a temperature below the glass transition temperature of the sample, and a part of the sample is kept below the glass transition temperature of the sample material throughout the method, as a result of which part of the sample stays vitrified.

4. The method of claim 1 in which the extremity is a metal extremity.

5. The method of claim 1 in which the extremity is vibrating while contact is made.

6. The method of claim 1 in which the frequency of the vibration is between 1 and 100 kHz.

7. The method of claim 1 in which the amplitude of the vibration at the extremity is between 10 and 200 nm.

8. The method of claim 1 in which the extremity vibrates in a plane parallel to the surface of the sample.

9. The method of claim 1 in which the welding takes place in an evacuated sample chamber of a charged particle apparatus.

10. The method of claim 9 in which the charged particle apparatus comprises an electron column or a focused ion beam column.

11. A microprobe for use with a charged particle apparatus, the charged particle apparatus having a stage equipped to hold a sample, the microprobe having an extremity, the microprobe equipped with positioning means to bring the extremity in contact with the sample, wherein the extremity is equipped to vibrate for locally melting the sample when vibrating and in which the extremity is adapted to be cooled to a temperature below the glass transition temperature of vitreous ice.

12. A charged particle apparatus equipped with a focused ion beam column and/or an electron beam column, a stage equipped to hold a vitrified biological sample at a cryogenic temperature, the charged particle apparatus equipped with a microprobe having an extremity, the microprobe equipped with positioning means to bring the extremity in contact with the sample, wherein the extremity is equipped to vibrate for locally melting the sample when vibrating.

13. The charged particle apparatus of claim 12 equipped to keep the sample at a temperature below the glass transition temperature of vitreous ice, wherein the extremity is adapted to be cooled to a temperature below the glass transition temperature of vitreous ice.

14. The charged particle apparatus of claim 12 further comprising a system controller including instructions comprising:
  providing the sample;
  providing the microprobe with the extremity;
  moving the extremity to the sample until contact is made;
  locally melting the sample while a part of the sample is kept solidified; and
  freezing the locally melted sample to the extremity;
  wherein the local melting is achieved by vibration of the extremity, the locally melted sample freezing to the extremity when the vibration is stopped.

15. The charged particle apparatus of claim 14 in which the sample is a vitrified aqueous sample or a vitrified polymer, the sample is provided at a temperature below the glass transition temperature of the sample, and a part of the sample is kept below the glass transition temperature of the sample material throughout the method, as a result of which part of the sample stays vitrified.

16. The charged particle apparatus of claim 14 in which the extremity is vibrating while contact is made.

17. The charged particle apparatus of claim 14 in which the extremity vibrates in a plane parallel to the surface of the sample.

18. The charged particle apparatus of claim 14 in which the freezing takes place in an evacuated sample chamber of the charged particle apparatus.

19. The charged particle apparatus of claim 12 in which the extremity is a metal extremity.

* * * * *